United States Patent
Nino et al.

(10) Patent No.: US 9,931,741 B2
(45) Date of Patent: Apr. 3, 2018

(54) IN-LINE DISPOSABLE TORQUE LIMITING DEVICE SUITABLE FOR POWER DRIVE

(71) Applicant: ECA Medical Instruments, Newbury Park, CA (US)

(72) Inventors: John Nino, Simi Valley, CA (US); David Ivinson, Camarillo, CA (US)

(73) Assignee: ECA MEDICAL INSTRUMENTS, Newbury Park, CA (US)

( * ) Notice: Subject to any disclaimer, the term of this patent is extended or adjusted under 35 U.S.C. 154(b) by 250 days.

(21) Appl. No.: 14/806,126

(22) Filed: Jul. 22, 2015

(65) Prior Publication Data
US 2015/0321326 A1    Nov. 12, 2015

Related U.S. Application Data

(63) Continuation of application No. PCT/US2014/010550, filed on Jan. 14, 2014.
(Continued)

(51) Int. Cl.
*B25B 23/14* (2006.01)
*A61B 17/88* (2006.01)
(Continued)

(52) U.S. Cl.
CPC .... *B25B 23/141* (2013.01); *A61B 17/320016* (2013.01); *A61B 17/8875* (2013.01);
(Continued)

(58) Field of Classification Search
CPC . B25B 23/141; B25B 23/1427; B25B 23/147; B25B 23/1405; F16D 7/042;
(Continued)

(56) References Cited

U.S. PATENT DOCUMENTS 5,295,907 A    3/1994 Akkerman
6,132,435 A    10/2000 Young
(Continued)

FOREIGN PATENT DOCUMENTS

BE            498191 A    1/1951
WO    WO 2003/013372 A2    2/2003
(Continued)

OTHER PUBLICATIONS

European Patent Application No. 14743591.1; Office Action Rule 164(1)—Partial Search Report; dated Mar. 28, 2017; 6 pages.
(Continued)

*Primary Examiner* — David B Thomas
(74) *Attorney, Agent, or Firm* — Baker & Hostetler LLP

(57) ABSTRACT

A power driven in-line disposable torque-limiting device having a tool shaft extending axially through upper and lower shanks, and a spring to connect to a nut and a drive shaft, the tool shaft extending from the distal end of the device and a drive shaft extending from the proximal end of the device which mates with a power supply to provide rotational force, is disclosed. The face-to-floor gears within the device provide superior heat management capabilities, thereby reducing ablation and melting as compared to traditional gear arrangements. A fortified connector mount supports a power driven shaft.

13 Claims, 12 Drawing Sheets

Related U.S. Application Data

(60) Provisional application No. 61/755,882, filed on Jan. 23, 2013.

(51) Int. Cl.
| | | |
|---|---|---|
| *A61B 19/00* | (2006.01) | |
| *B25B 23/147* | (2006.01) | |
| *F16D 7/04* | (2006.01) | |
| *A61B 17/32* | (2006.01) | |
| *B25B 15/04* | (2006.01) | |
| *B25B 23/142* | (2006.01) | |
| *A61B 90/00* | (2016.01) | |

(52) U.S. Cl.
CPC .............. *A61B 90/03* (2016.02); *B25B 15/04* (2013.01); *B25B 23/147* (2013.01); *B25B 23/1427* (2013.01); *F16D 7/044* (2013.01); *A61B 2090/031* (2016.02)

(58) Field of Classification Search
CPC ............... F16D 7/044; F16D 2011/008; A61B 17/320016; A61B 17/8875; A61B 2090/031
See application file for complete search history.

(56) References Cited

U.S. PATENT DOCUMENTS

| | | | | |
|---|---|---|---|---|
| 7,334,509 | B1* | 2/2008 | Gao | B25B 15/02 |
| | | | | 81/467 |
| 8,220,369 | B2* | 7/2012 | Lai | B25B 13/06 |
| | | | | 81/471 |
| 8,808,095 | B2* | 8/2014 | Cheng | F16D 7/044 |
| | | | | 464/23 |
| 8,973,728 | B1* | 3/2015 | York | F16D 7/044 |
| | | | | 192/56.61 |
| 9,095,964 | B2* | 8/2015 | Ivinson | B25B 13/46 |
| 9,132,536 | B2* | 9/2015 | Nino | A61B 17/8883 |
| 9,162,350 | B2* | 10/2015 | Nino | B25B 15/04 |
| 9,241,751 | B2* | 1/2016 | Nino | B25B 13/466 |
| 9,242,357 | B2* | 1/2016 | Nino | B25B 23/141 |
| 9,259,258 | B2* | 2/2016 | Laurenti | B25B 23/1427 |
| 9,445,873 | B2* | 9/2016 | Nino | A61B 17/8883 |
| 2008/0271576 | A1* | 11/2008 | Hsieh | B25B 13/06 |
| | | | | 81/121.1 |
| 2009/0145568 | A1* | 6/2009 | Chaterjee | B25B 23/141 |
| | | | | 164/57.1 |
| 2009/0194307 | A1* | 8/2009 | Rinner | B25B 23/1427 |
| | | | | 173/181 |
| 2010/0274230 | A1 | 10/2010 | Edgell et al. | |
| 2011/0000347 | A1 | 1/2011 | Stark | |
| 2011/0056341 | A1* | 3/2011 | Lai | B25B 13/06 |
| | | | | 81/475 |
| 2012/0198972 | A1 | 8/2012 | Nino et al. | |
| 2012/0291599 | A1 | 11/2012 | Cutler | |
| 2013/0226192 | A1* | 8/2013 | Nino | B25B 13/466 |
| | | | | 606/104 |
| 2013/0319190 | A1* | 12/2013 | Nino | B25B 23/141 |
| | | | | 81/475 |
| 2015/0148176 | A1 | 5/2015 | Schroeder et al. | |
| 2016/0030101 | A1* | 2/2016 | Nino | B25B 15/04 |
| | | | | 81/475 |

FOREIGN PATENT DOCUMENTS

| | | |
|---|---|---|
| WO | WO 2012/015660 A2 | 2/2012 |
| WO | WO 2012/112591 A2 | 8/2012 |

OTHER PUBLICATIONS

International Patent Application No. PCT/US2014/010550; Int'l Preliminary Report on Patentability; dated Aug. 6, 2015; 11 pages.
European Patent Application No. 14743591.1; Supplemental Search Report; dated Sep. 22, 2017; 5 pages.

\* cited by examiner

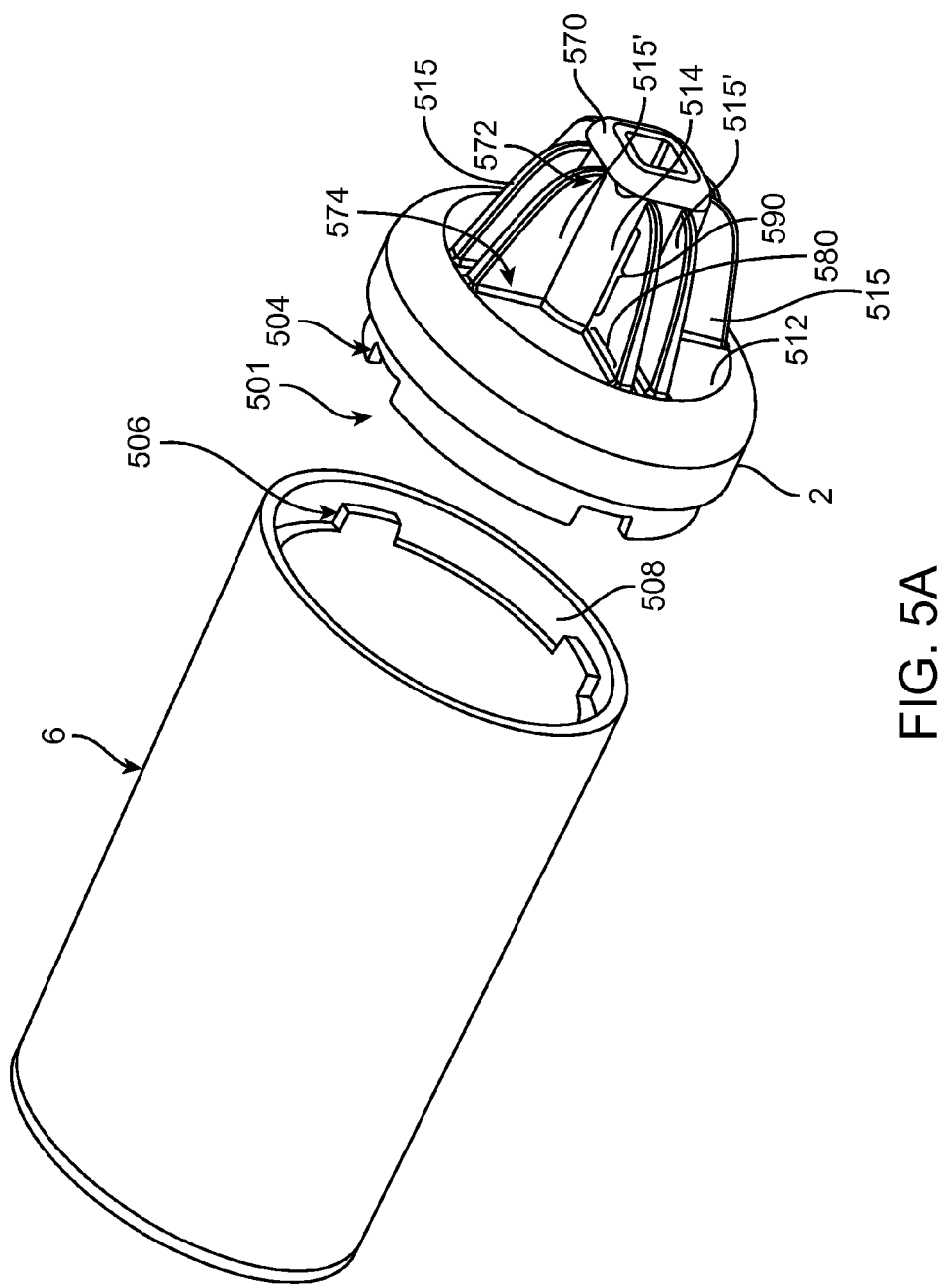

IN-LINE DISPOSABLE TORQUE LIMITING DEVICE SUITABLE FOR POWER DRIVE

CROSS REFERENCE TO RELATED APPLICATIONS

This Utility patent application is a Continuation of International patent application PCT/US2014/010550 filed Jan. 7, 2014, which claims the full Paris Convention benefit of and priority to U.S. provisional application No. 61/755,882 filed Jan. 23, 2013, the contents of which are incorporated by this reference as if fully set forth herein in their entirety.

BACKGROUND

1. Field

This disclosure relates to an inline disposable driver tool with plastic gear drive and, in particular, to a medical use torque-limiting driver that disengages at a predetermined torque limit.

2. General Background

Torque is a measure of force acting on an object that causes that object to rotate. In the case of a driver and a fastener, this measurement can be calculated mathematically in terms of the cross product of specific vectors:

$$\tau = r \times F$$

Where r is the vector representing the distance and direction from an axis of a fastener to a point where the force is applied and F is the force vector acting on the driver.

Torque has dimensions of force times distance and the SI unit of torque is the Newton meter (N-m). The joule, which is the SI unit for energy or work, is also defined as an N-m, but this unit is not used for torque. Since energy can be thought of as the result of force times distance, energy is always a scalar whereas torque is force cross-distance and so is a vector-valued quantity. Other non-SI units of torque include pound-force-feet, foot-pounds-force, ounce-force-inches, meter-kilograms-force, inch-ounces or inch-pounds.

Torque-limiting drivers are widely used throughout the medical industry. These torque-limiting drivers have a factory pre-set torque to ensure the accuracy and toughness required to meet a demanding surgical environment.

The medical industry has made use of both reusable and disposable torque-limiting drivers. In a surgical context, there is little room for error and these drivers must impart a precise amount of torque.

Reusable drivers require constant recalibration to ensure that the driver is imparting the precise amount of torque. Recalibration is a cumbersome task but must be done routinely. Such reusable devices also require sterilization.

Disposable drivers are an alternative to the reusable drivers. Once the driver has been used, it is discarded.

Disposable drivers are traditionally used for low torque applications. The standard torque values in these applications typically range from about 4 to about 20 inch-ounces. It has, however, been a challenge to develop a reliable disposable driver capable of imparting higher torques for larger applications.

Piecemeal drivetrain systems have been developed to gear-up or otherwise impart greater torque with disposable devices. Such piecemeal systems provide interchangeability of parts to a device, within which torque is transferred from part-to-part of a piecemeal system.

SUMMARY

U.S. Provisional Patent Application Ser. No. 61/755,640 filed concurrently herewith is hereby incorporated by this reference as if fully set forth herein in its entirety.

A motor powered torque-limiting driver, in accordance with the present disclosure of a device and method, having a cylindrical body with a fortified connector mount on one end and a nose cone at the other end; a drive shaft for connection to a motor for rotating the nose cone is affixed to the connector mount; the body contains an upper shank having a face to floor (FtF) crown gear around an axial bore and a lower cylindrical shank having a FtF crown gear around a drive socket. Placing the crown gears of the upper and lower shank face to face constructs a clutch mechanism as follows: a shaft having a tip, a drive connection and a threading is engaged within the drive socket of the lower cylindrical shank, the shaft extending through the axial bore of the upper shank with a nut of a size and thread to mount on said threading and a spring between the upper shank and nut, wherein the spring is configured to apply a force across the upper cylindrical shank and the lower cylindrical shank; and the spring and connected via the threading to the nut; and, wherein the upper cylindrical shank and the lower cylindrical shank engage for relative rotation when a motor applies rotational force to the drive shaft, and wherein the upper cylindrical shank and the lower cylindrical shank disengage when a predetermined torque limit is exceeded. In some instances the torque-limiting driver's fortified connector mount further comprises a drive cap having pairs of opposing force buttressing ribs force "FBRs" affixed at one edge to an annular wall surrounding the connector mount and at another edge affixed to a flat top of the cap.

A motor powered torque-limiting driver, in accordance with the present disclosure of a device and method wherein a force provided by the spring securely maintains the drive connection of the shaft engaged within the drive socket of the lower cylindrical shank.

A motor powered torque-limiting driver, in accordance with the present disclosure of a device and method wherein the predetermined torque limit is between about 20 inch-pounds and about 50 inch-pounds.

A motor powered torque-limiting driver, in accordance with the present disclosure of a device and method wherein the driver applies a force of between about 20 inch-pounds and about 50 inch-pounds at an RPM exceeding 350 RPM.

A motor powered torque-limiting driver, in accordance with the present disclosure of a device and method wherein the driver applies a force of between about 20 inch-pounds and about 50 inch-pounds at an RPM exceeding about 500 RPM.

A motor powered torque-limiting driver, in accordance with the present disclosure of a device and method wherein the driver applies a force of between about 20 inch-pounds and about 50 inch-pounds at an RPM between about 250 RPM and about 600 RPM.

A crown gear for a motor powered torque-limiting driver, in accordance with the present disclosure of a device and method having a cylindrical shank with an outer cylindrical shank wall and an axial bore and formed circularly around said axial bore a series of raised plateaus each with a leading edge interspersed between a series of floors.

A clutch for a motor powered torque-limiting driver, in accordance with the present disclosure of a device having a lower cylindrical shank with an drive socket mated with an upper cylindrical shank having an axial bore and face to floor (FtF) raised plateaus formed circularly around each of said axial bore and said drive socket; each FtF having a leading edge interspersed between a series of floors.

DRAWINGS

The above-mentioned features of the present disclosure will become more apparent with reference to the following description taken in conjunction with the accompanying drawings wherein like reference numerals denote like elements and in which:

FIGS. 5A-5B show an exploded view of some aspects of a powered in-line torque liming driver, a fortified connector mount and a top view of the connector mount;

Figure 4A:
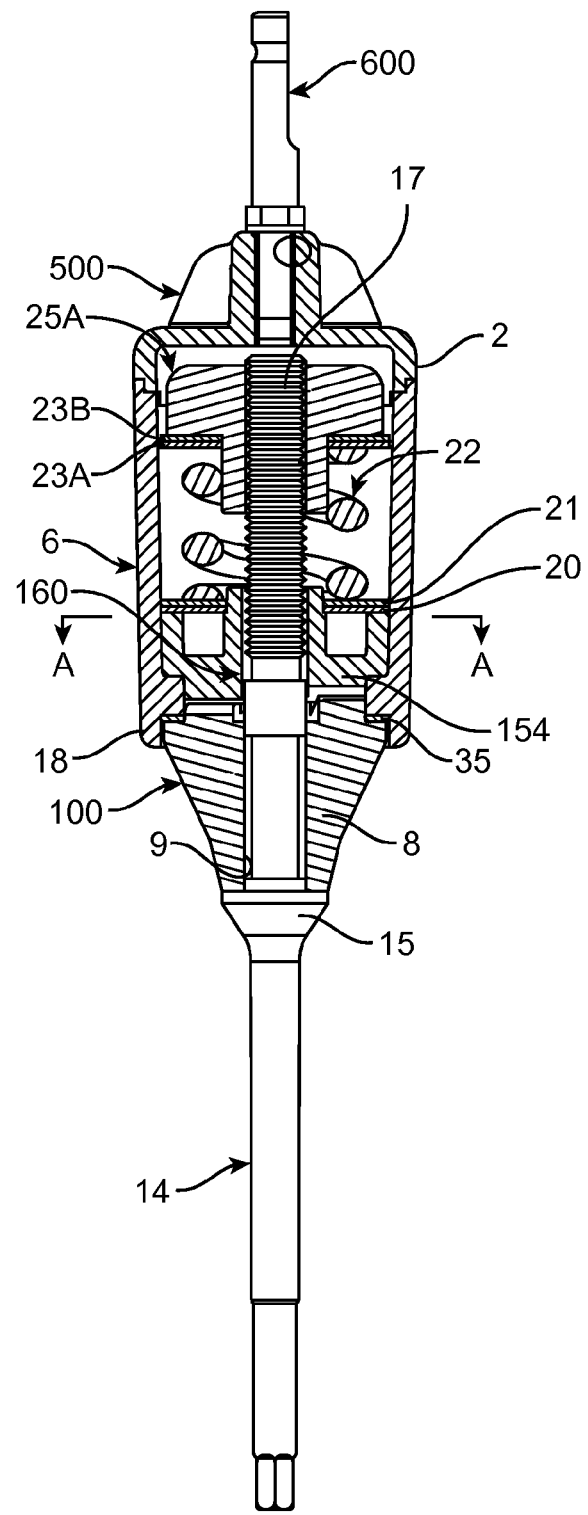
FIG. 4A shows an cutaway view of some aspects of a powered in-line torque liming driver.

The Appendix shows a variation of the powered torque limiting device of FIG. 4A with a cup washer.

While the specification concludes with claims defining the features of the present disclosure that are regarded as novel, it is believed that the present disclosure's teachings will be better understood from a consideration of the following description in conjunction with the appendices, figures, in which like reference numerals are carried forward. All descriptions and callouts in the Figures and Appendix are hereby incorporated by this reference as if fully set forth herein.

FURTHER DESCRIPTION

According to one or more exemplary implementations, as shown in FIGS. 1-6 and 8, aspects of inline torque-limiting drivers are disclosed.

A powered in-line torque limiting driver 1 may have a generally cylindrical body with a cup shaped drive cap 2 or other structure to facilitate use by a user. For example, the drive cap is affixed to a generally hollow cylindrical body 6. Cylindrical distal end 18 terminates cylindrical body 6 toward tip 12 of tool shaft 14. Cap 2 is mated to the cylindrical body at the proximal end 19 of the cylindrical body the cap 2 may be snap-fitted to cylindrical body 6, or may be welded, adhered, or attached by any equivalent thereof. A connector mount 500 is shown formed on the cap. The connector mount 500 provides a fixation of a drive shaft 600 for a powered in-line torque limited driver. The power source is preferably an electric motor. The motor may apply at least one of force and rotational speed in excess of a human operator. In use, the drive shaft imparts rotational force to the connector mount 500 which is fixed to the cap 2 and body 6 thereby rotating engaged crown gears within the body and rotating the nose cone 8 and attached tool 12.

Exemplary implementation show, at least in part, at cylindrical distal end 18, lower shank 100 having an annularly tapering body and nose cone 8 along its length. Lower shank 100 may have a plurality of support flanges 10 that add strength while saving material. At one end, lower shank 100 tapers to drive socket 9 at the end of the nose cone 8 molded to engage drive connection 16 of tool shaft 14. An exemplary implementation shows, at least in part, shaft 14 provided, at one end, with workpiece-engaging tip 12, adapted for engagement with an associated workpiece, such as a fastener or the like. Workpiece-engaging tip 12 is shown to be a hex type wrench but could be a screwdriver, wrench, socket wrench, or any other tool arrangement. At an opposite end, lower shank 100 has a plurality of teeth 200 arranged in a crown gear formation, with circumferential rim 30 extending radially outward and an internal axial bore to accommodate at least a portion of shaft 14 extending there through.

Figure 4B:
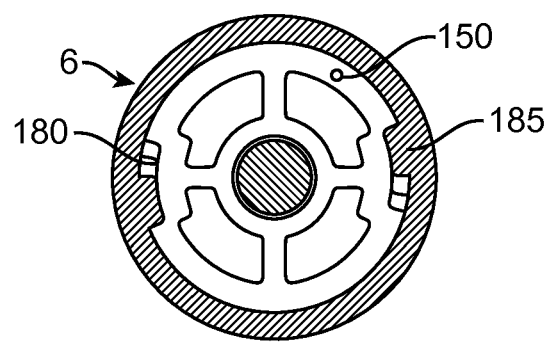
FIG. 4B shows a drive spline along line A-A of FIG. 4A.

According to aspects of one or more exemplary implementations, inside cylindrical body 6 a clutch assembly is disposed. The clutch assembly 240 includes upper shank 150 for forcibly engaging lower shank 100. Upper shank 150 has a bottom face that has a plurality of teeth 250 arranged in a crown gear formation and circumferential rim 152 extending radially outward. As shown in FIGS. 4A and 4B, upper shank 150 includes an annular outer cylindrical shank wall 154 and an axial bore 160.

Figure 6:
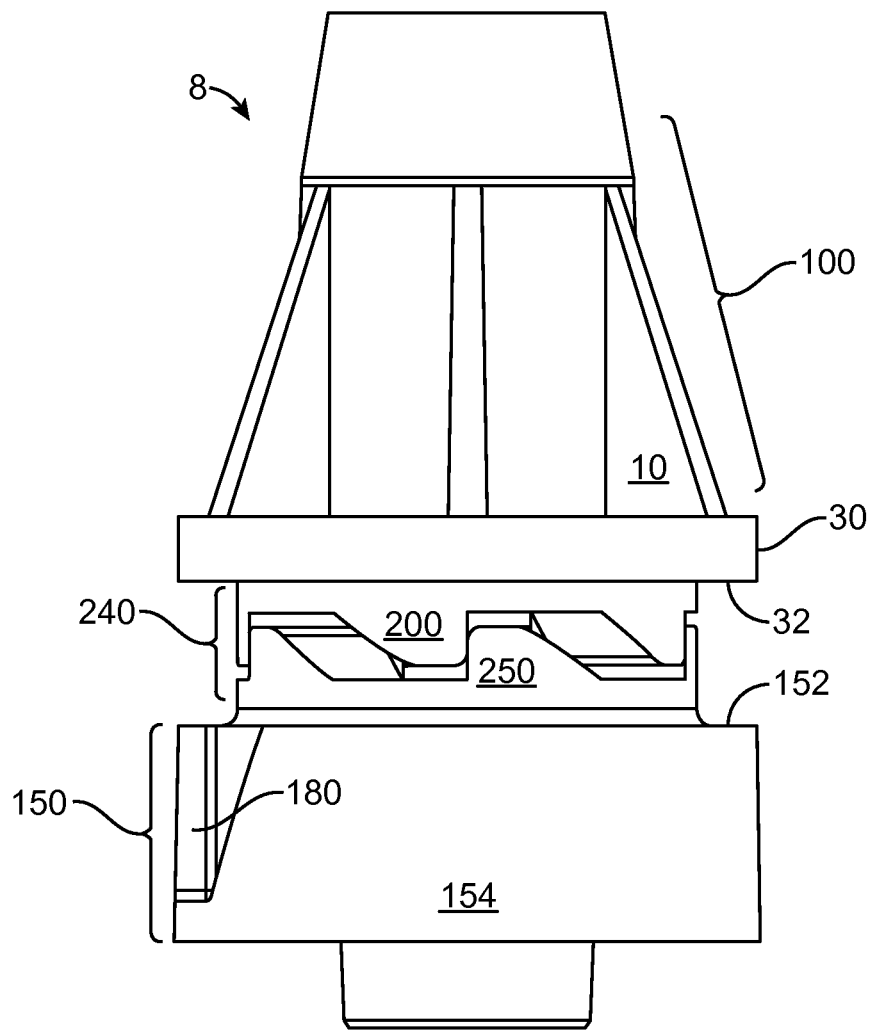
FIG. 6 shows a component view of the drive clutch assembly of a powered in-line torque liming driver.

According to one or more exemplary implementations, upper shank 150 includes at least one recess 180 on a side of the annular outer cylindrical shank wall 154. Recess 180 is provided as a cylindrical cut, relief or recess into the side of the outer shank and maybe provided as a square or rectangular cut or the cut may have a slanted side or sides relative to the axis of upper shank 150, as shown in FIGS. 6 and 8.

In assembly, drive connection 16 of tool shaft 14 is received into drive socket 9 of lower shank 100. In some instance a square drive socket 9 is preferred and the drive connection is a corresponding shape. Washer 35 maybe provided between the bearing surface of circumferential rim 32 of lower shank 100 and a circumferential flange 33 extending radially inward within the hollow of cylindrical body 6. Washer 35 may be of a polymer or other material having low coefficient of friction. Alternatively, circumferential rim 32 of lower shank 100 may be provided flush against circumferential flange 33 of cylindrical body 6. The opposite side of circumferential flange 33 receives circumferential rim 152 of upper shank 150, allowing teeth 200 of lower shank 100 to engage teeth 250 of upper shank 150 when a torque is applied.

According to aspects of one or more exemplary implementations, integrally formed within cylindrical body 6, protrusion 185 mates with recess 180 of upper shank 150. FIG. 4B illustrate protrusion 185 in relation with recess 180. Protrusion 185 extends inward in a radial fashion and has a length along the axis of cylindrical body 6 for relative moveable engagement within recess 180. This engagement provides a locking mechanism of shaft 14 relative to the handle via upper shank 150 when pressure is applied across lower shank 100 and upper shank 150. Recess 180 is provided circumferentially wider than protrusion 185 for allowing cylindrical body 6 and the cap 2 to rotate in reverse a predetermined distance from a locked position without subsequent reverse rotation of workpiece-engaging tip 12. Thus, at least one recess 180 and at least one protrusion 185 lock the body in one direction providing the necessary torque to drive a fastener and allow for a predetermined amount of reverse rotation before unscrewing the fastener.

According to aspects of one or more exemplary implementations, force is applied across lower shank 100 and upper shank 150 via spring 22 within cylindrical body 6. Inside cylindrical body 6, shown in FIG. 3 and FIG. 4A, washer one 20 and washer two 21 are provided between upper shank 150 and spring 22. The washers transfer pressure from spring 22 over the top face of upper shank 150. Shown in FIGS. 3 and 4A at an end of spring 22 opposite upper shank 150, washer three 23 and nut 25A hold spring 22 in a relatively compressed state. Washer 23 may be provided between nut 25A and spring 22 to facilitate relative rotation of nut 25A and spring 22. Nut 25A is formed of material softer than shaft 14, nut 25A has an unobstructed open center 26 with a diameter smaller than the diameter of shaft 14 and a smooth surface malleable enough to be deformed by the rotational insertion to said open center 26 of the threading 17 at an end of shaft 14. The Appendix shows a variation of the device wherein a cup washer replaces nut 25A.

According to aspects of one or more exemplary implementations, enhanced nut 25A may provide an upper shoulder portion 25B having a diameter larger than the inner diameter of spring 22 and a lower neck portion 25C having outer diameter substantially equal to an inner diameter of spring 22. The lower neck portion 25C of nut 25A may extend axially through at least a portion of spring 22. At least one of the upper shoulder portion 25B and the lower neck portion 25C of nut 25A may maintain relative axial alignment between nut 25A and spring 22 by limiting travel of spring 22 other than by compression thereof.

Closing the handle and device is a cap 2. The cap supports a mount 500, which may be fortified as detailed in applicant's co-pending, same day filed, applications entitled "Fortified Plastic Connector Mount for Disposable Devices," U.S. provisional application No. 61/755,640 Those of ordinary skill in the art will recognize that a variety of mounts may be utilized to support a drive shaft 600 and the illustration of a fortified mount is not a limitation.

According to aspects of one or more exemplary implementations, various materials may be used for the components of driver 1. According to some exemplary implementations, at least one of body 6, nut 25A, lower shank 100, and upper shank 150 is of a plastic material or a composite including plastic. Plastic and other economical equivalents improve cost efficiency of production while providing high tensile strength, resistance to deformation, etc. Effective materials include plastics, resins, polymers, imides, fluoropolymers, thermoplastic polymers, thermosetting plastics, and the like as well as blends or mixtures thereof. According to aspects of one or more exemplary implementations, at least one of lower shank 100 and upper shank 150 is of or includes at least one material that lubricous or otherwise reduces friction. The presence of a friction-reducing material allows geometric aspects of the engagement between lower shank 100 and upper shank 150 to govern whether teeth engage or disengage, thereby improving precision of the device.

According to aspects of one or more exemplary implementations, materials and components of disposable in-line driver 1 are resistant to sterilization, cleaning, and preparation operations. For example, driver 1 and parts thereof are configured to withstand sterilization by methods including radiation (e.g., gamma rays, electron beam processing), steam (e.g., autoclave), detergents, chemical (e.g., Ethylene Oxide), heat, pressure, inter alia. For example, materials may be selected according to resistance to one or more selected sterilization techniques.

According to aspects of one or more exemplary implementations, shaft 14 is of a rigid material. For example, shaft 14 may be of a metal, such as stainless steel. According to some exemplary implementations, high torque capabilities of driver 1 are, at least in part, provided by features that maintain an effective engagement between drive connection 16 of shaft 14 and drive socket 9 of lower shank 100. For example, some exemplary implementations are provided to improve the ability of driver 1 to maintain its grip on shaft 14 up to a greater range of torque.

According to aspects of one or more exemplary implementations, a single integrated shaft 14 spans the distance between workpiece-engaging tip 12 and an engagement point with nut 25A. This configuration enables greater torque capabilities than a piecemeal or fragmented set of interconnected components. This reduces the number of interconnections between a source of a torque and a location to which the torque is transferred.

According to one or more exemplary implementations, shaft 14 having drive connection 16 between opposing extensions stabilizes drive connection 16 within drive socket 9. Placement of drive connection 16 at a medial segment of shaft 14—rather than at an end thereof—facilitates a more stable engagement between drive connection 16 and drive socket 9, thereby increasing the ability of engagement to transfer high amounts of torque.

According to one or more exemplary implementations, an engagement of drive connection 16 within drive socket 9 is maintained by the connection of the integrated portion of shaft 14 that extends to nut 25A. According to some exemplary implementations, both threading 17 and drive connection 16 are of a single integrated structure (i.e., shaft 14). A force applied by spring 22 to nut 25A is directly transferred along shaft 14 from threading 17 to drive connection 16. This force securely maintains drive connection 16 within drive socket 9. This engagement enables transfers of greater amounts of torque from upper shank 150 to lower shank 100 (i.e., via drive socket 9) to shaft 14 (i.e., via drive connection 16).

According to aspects of some exemplary implementations, drive connection 16 and drive socket 9 have complementary geometries. One or more of a variety of configurations may be provided for engaging drive connection 16 within drive socket 9. For example drives and associated connections may include triangular, square, hexagonal, rectangular, etc. According to aspects of one or more exemplary implementations, a substantially square drive connection 16 and drive socket 9 provide high torque transfer capabilities. Out of a variety of drive types, experimental results demonstrated that square drives and connections were among the most successful at transferring high torque without failure. Drive connection 16 and drive socket 9 may have rounded corners and edges to reduce or distribute stress risers.

Figure 1:
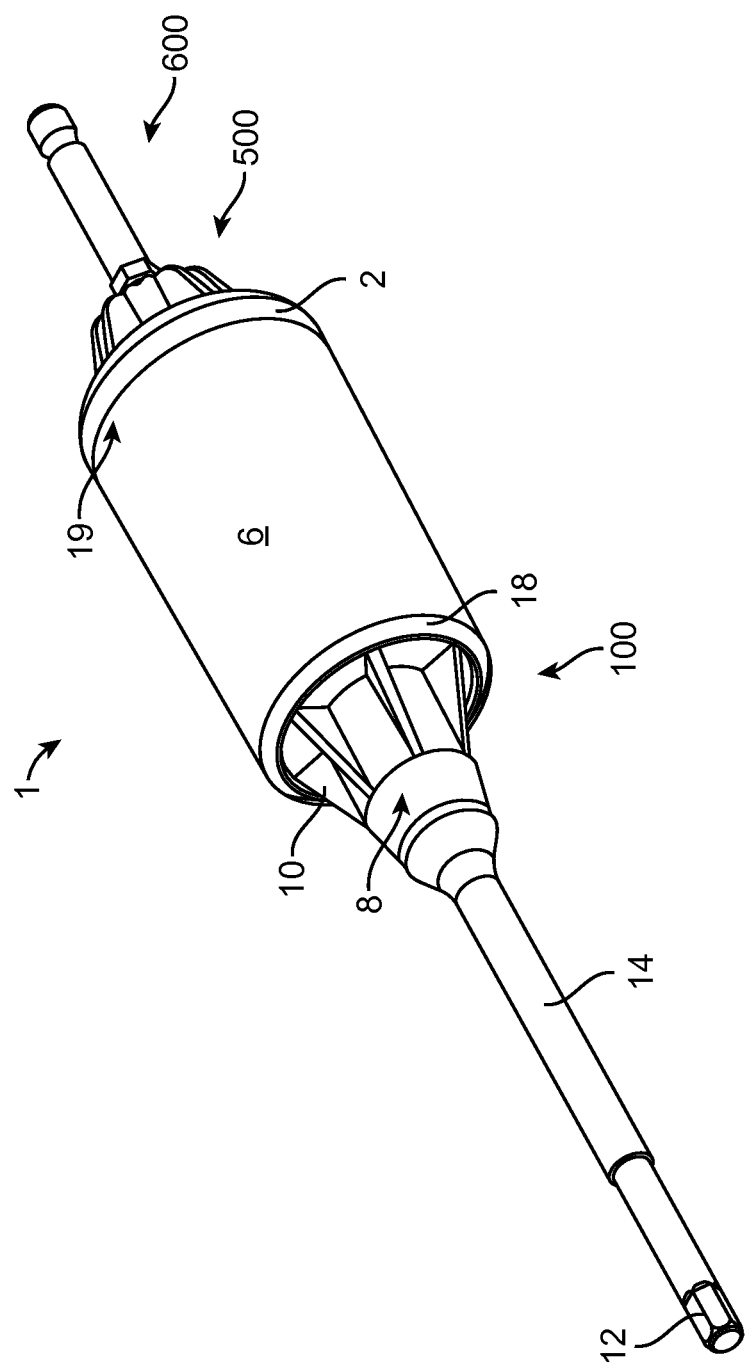
FIG. 1 shows a perspective front to back view of some aspects of a powered in-line torque liming driver.
Figure 2:
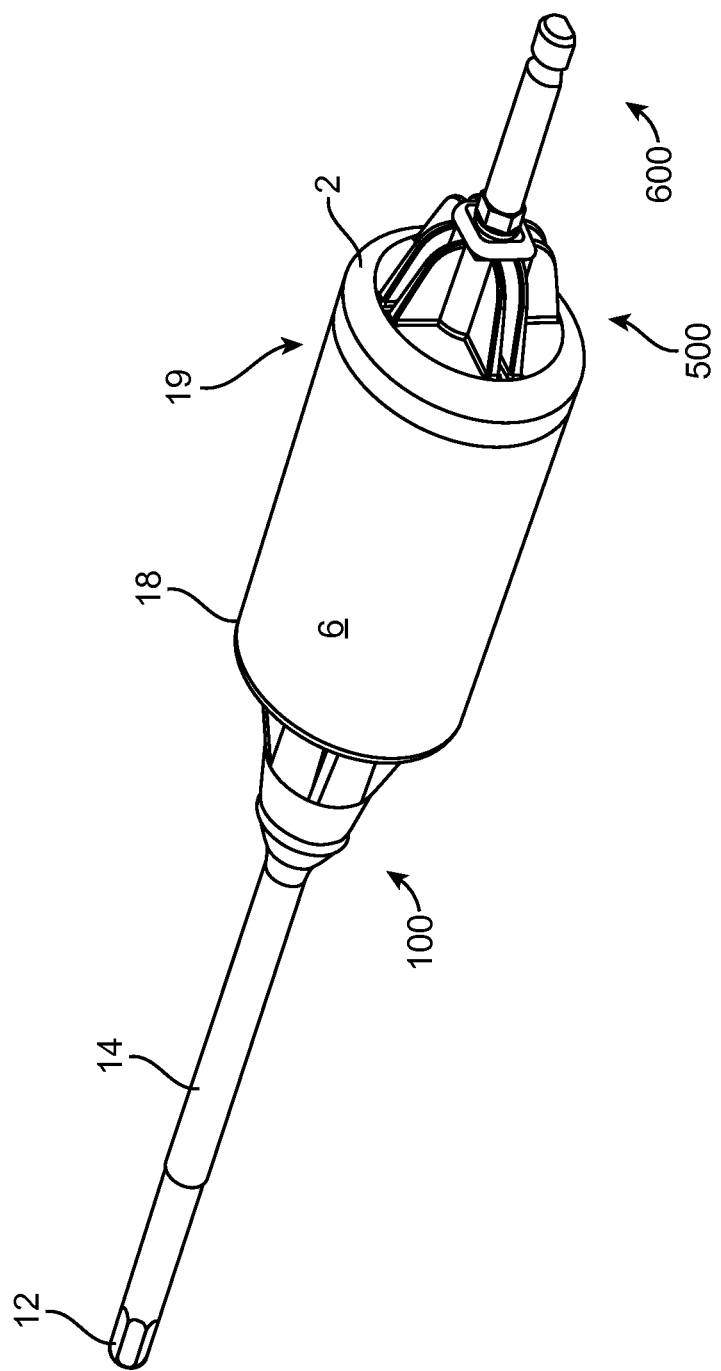
FIG. 2 shows a perspective back to front view of some aspects of a powered in-line torque limiting driver.
Figure 3:
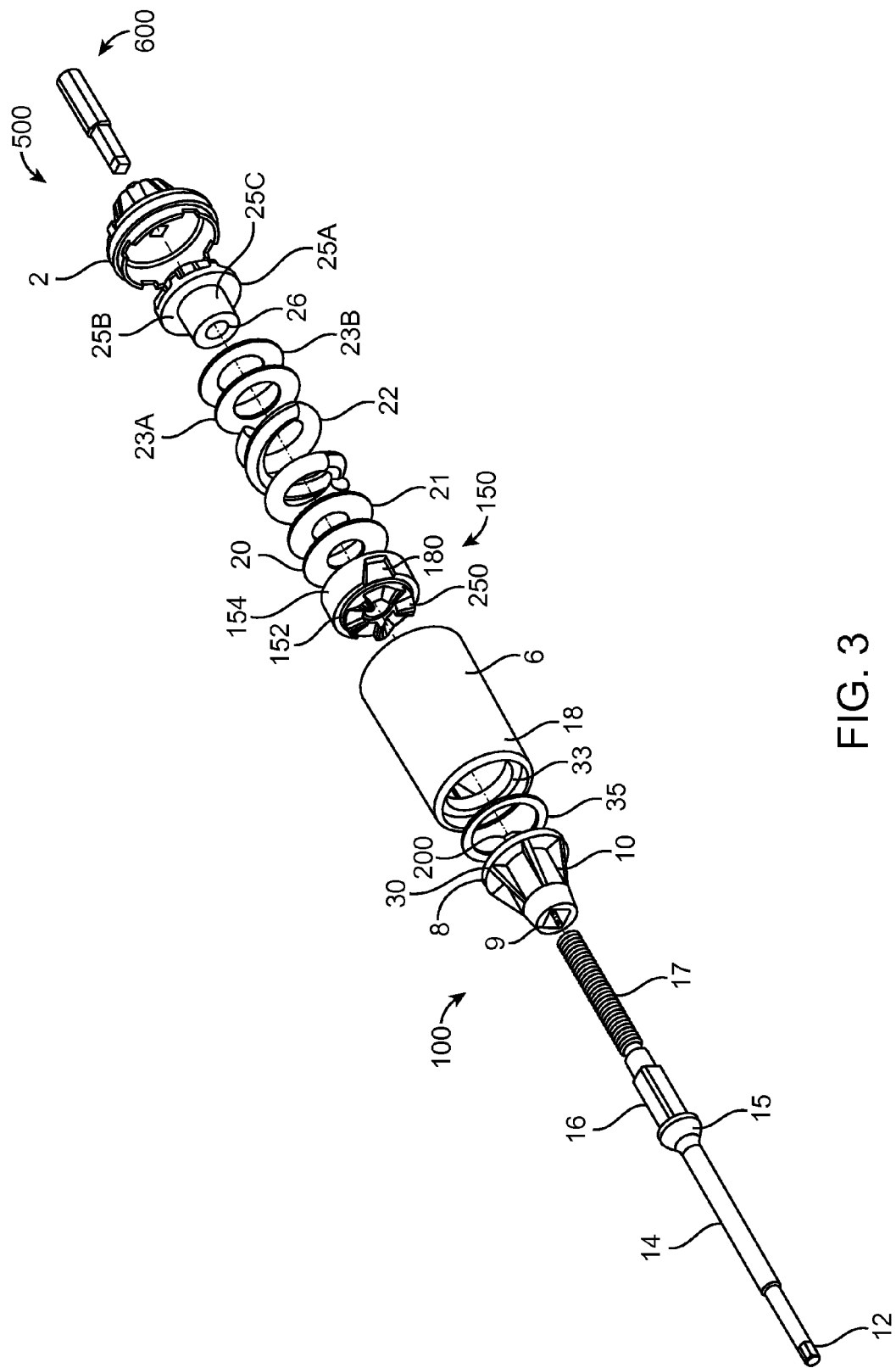
FIG. 3 is an assembly view of a powered in-line torque limiting driver.
Figure 5B:
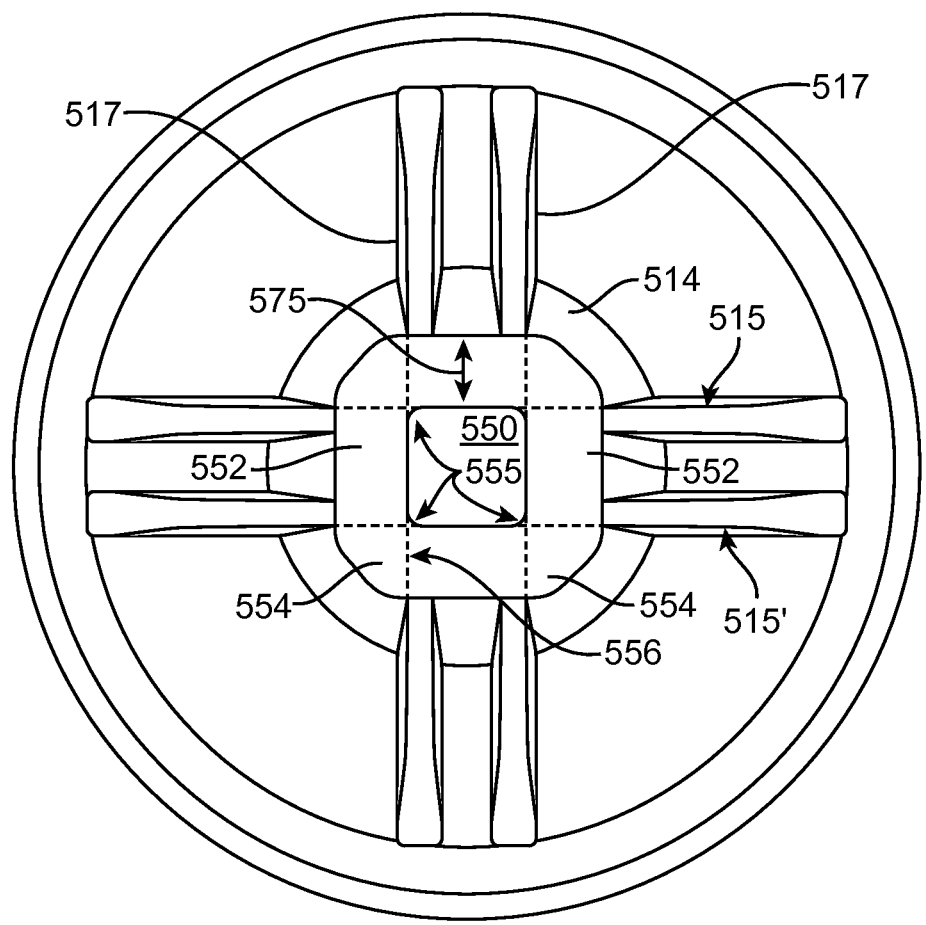

Referring now to FIGS. 3, 5A & 5B the cap 2 may also be referred to as a drive cap. It has a distal end 501 and a proximal end 502. The drive cap 2 is both a cover for the body and supports, as part thereof, a mounting fixture and drive. The cap 2 transfers the rotational force from the drive shaft 600 to the body 6. The drive cap is generally circular in cross section. At its cylindrical distal end 501 are formed one or more drive notches 504 which mates with one or more drive teeth 506 formed along the inner annular wall 508 of the handle. Said cap may be snap-fitted to cylindrical body 6, or may be welded, adhered, or attached by any equivalent thereof. The plastic molded fortified connector mount "CM" 500 provides a guide and/or anchor to mount, fix or connect tools and/or other connectors to the device 1. The CM mount has a generally conical nose, affixed to a body 6. The cap 2 is generally cylindrical and has a flat top 512. The nose CM 500 has an annular outer wall 514.

A CM is supports or encases a shaft (not shown) which mates to a drive channel forming a shaft guide 550. The drive channel will hold fast a shaft against a force applied via rotation of the nose 500 and body 6. Sets of force buttressing ribs (FBR) 515 & 515' are positioned around the outer annular wall 514. The force buttressing ribs provide support to the outer annular wall 514 by distributing the load from said wall to the flat top 512. FBRs are positioned to be aligned with an edge or side of the drive channel 550 opening, as well as each corner 555. The FBR brace each corner whether the unit is being rotated clockwise or counter-clockwise, so the FBR is preferably in-line with each side of each corner. These FBRs are at 90-degrees apart due to being at 180-degrees to the side of each opening they support. Being at 90-degrees and 180-degrees ensures that each side wall zone 552 and each corner zone 554 is equally braced.

The nose CM 500 is fortified or buttressed against shearing and other forces via very the specifically placed FBRs. The annular wall structure of the nose between the annular outer wall 514 and the channel 550 is also referred to as a boundary wall 570 and it can be separated into alternating zones. Zone 1 is a side wall zone 552, Zone 2 is the corner zone 554 and each zone is separated by a fortifications 556 located substantially directly between each channel corner 555, the annular wall 514 and the outer edge 517 of each rib. The boundary wall 570 is generally the same thickness 575 from drive channel 550 to the annular wall 514. However in some instances the thickness can vary as one moves from the distal end 572 of the nose toward the flat top 512. In some instances, the thickness of boundary wall 570 is preferably substantially the same cross sectional thickness between fortifications 556.

FBRs may be positioned at angles other than 90-degrees or 180-degrees, however, there will be an unbalanced situation where one side could be weaker than the other side, and therefore not reinforcing the adjacent zone adequately to withstand the highest force requirement. Such other angles may be acceptable in lower force situations, and are within the scope of this disclosure for such situations. A plastic nose material will eventually crack if force beyond the limits of the use intended is applied. By placing each FRB at a 90-degree angle from its base, the 90-degree angle achieves a balance force load, so that each side of rib receives equal force and therefore eliminates the unbalance. Each FBR spans from the annular wall to a flat top of the cap. Accordingly, FBR has a bottom 580 region affixed to, or formed as part of, the flat top 512 and each FBR has a side support edge 590 affixed to the annular wall 514.

FIG. 6 illustrates the engagement of the teeth of the drive system of the driver. The upper shank 150 and the lower shank 100 each have gear teeth facing one another. Upper shank teeth 250 engage lower shank 100 teeth 200. Until the torque limit is met the teeth in this crown gear arrangement will remain engaged. When the torque limit is met the spring 22 compre4sses and the teeth will slip thereby limiting the torque applied.

Figure 7A:
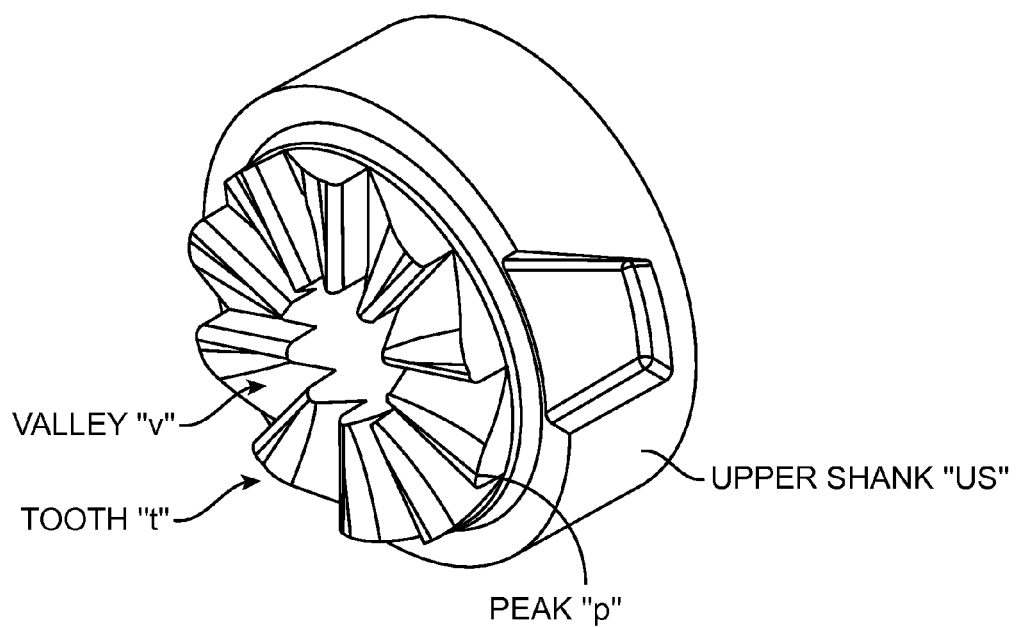
FIGS. 7A and 7B shows a traditional a drive gear of a plastic gear assembly of a powered in-line torque limiting device; and, FIGS. 8A and 8B show a plastic drive gear of a gear assembly of the powered in-line torque limiting device disclosed herein.
Figure 7B:
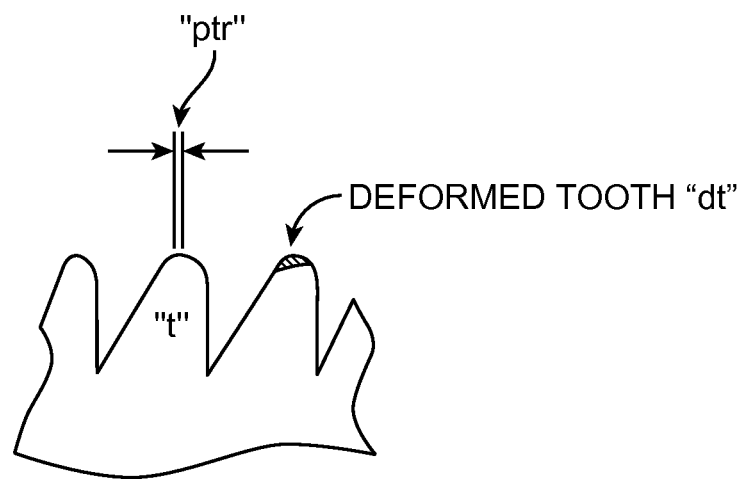

Traditionally, the plastic drive teeth are a peak "p" and valley "v" formation such as that shown in FIGS. 7A and 7B. One challenge facing the acceptance and use of plastic crown gears in a power driven torque limiting device has been that when the teeth of the upper shank and the teeth of the lower shank slip at the torque limit the peak tip region "ptr" of each tooth "t" is beaten or otherwise impacted by the teeth of the opposing gear. In the case of a power driven device experimental results have shown that the impact of opposing teeth when a disposable device is power driven tends to be many revolutions resulting in many impacts. The impacts cause one or more of heat, friction, deformation, ablation, melting of the "tpr" whereby a tooth becomes a deformed tooth "dt". Such deformed teeth result in the torque limit of the device changing. Accordingly, during multiple uses of a traditional torque limiting device utilizing the peak and valley gear configuration the torque imparted may decrease after the teeth become deformed whereby few duty cycles are available. A traditional 10-tooth crown gear and clutch formed therefrom was tested at three different motorized RPM speeds, started at slow speed of about 50 RPM then increased to medium speed of about 250 RPM then increased to fast speed of about 600 RPM. The faster the RPM the more erratic the torque actuation, in part due to the teeth not fully engage and in part due to the speed creating enough friction to heat the material causing deformation of the tooth profile, whereby the teeth where less engaging. The deformed teeth significantly impact the mechanism being able to achieve the set torque value, and achieve it repeatably within a specified tolerance and/or RPM. The traditional device failed to remain engage in any meaningful way at between 250 RPM and 600 RPM, was even less engaging between 350 RPM and 600 RPM Moreover, in testing the traditional clutch had a maximum torque limit of 20 inch-pounds before it degraded and eventually failed.

Figure 8A:
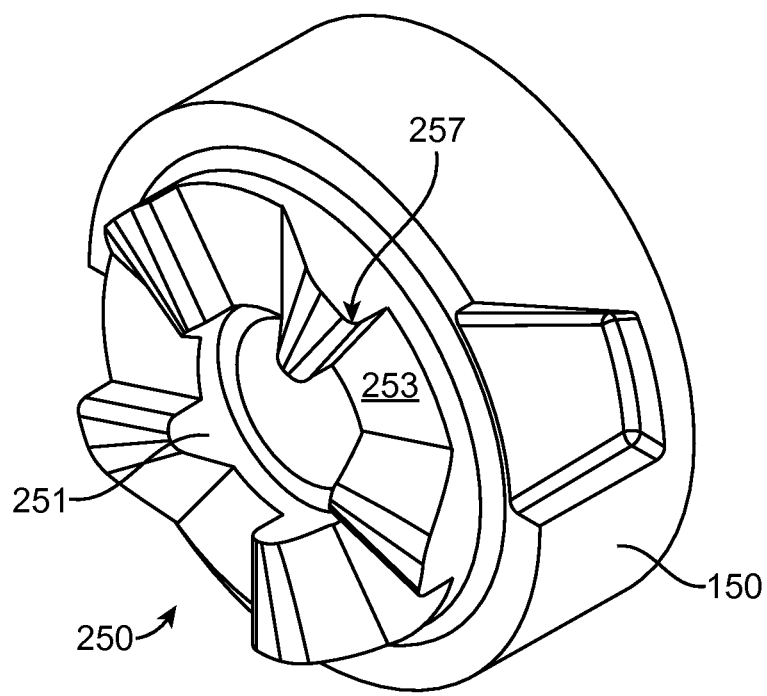
Figure 8B:
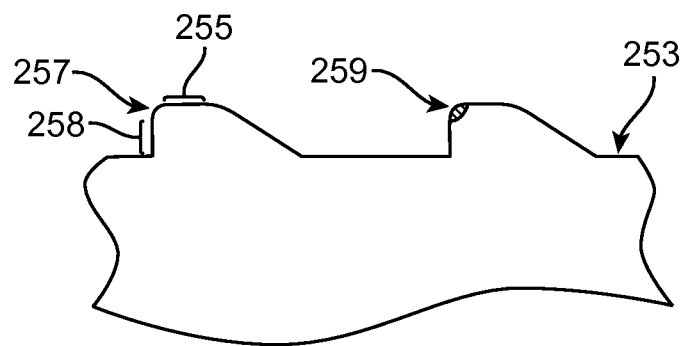

A face to floor (FtF) arrangement of crown gear teeth is disclosed herein. In FIGS. 8A and 8B. FIG. 8A shows the upper shank 150 of the device and the lower shank 100 has a matching crown gear. Each crown gear is formed around a bore, it is an alternating arrangement of raised plateaus 251 each with substantially flat faces 255 and separated by substantially flat floor portions 253. Additionally, each raised plateau to a substantially flat face rather than a peak or tip. Each face 255 has a leading edge 257 where the face meets the front wall 258 of the raised plateau 251. The leading edge is subject to friction and impact during operation of a torque limiting clutch 240 formed of two such crown gears. Similar to the traditional crown gear, even the FtF arrangement will suffer some deformation 259 of each tooth after impact with opposing teeth when the torque limits are met. However the mass of the plateau works as at least one of a buttress and a heat sink to reduce the melting of teeth and the deformed area is far less than in a traditional arrangement. When two FtF crown gears are mated to form a clutch 240, that FTF clutch mechanism (when tested at the three different motorized RPM speeds tested with the traditional 10 tooth clutch) performed measurably better.

The FtF arrangement has a thick, blunt plateau as compared to the narrow peaked traditional teeth, and although there are less teeth in such a FtF crown gear to form the interface of the clutch, and intuitively the more teeth should work better, because of the friction caused by use and the pounding of teeth against teeth when driven at high RPMs with a motor, the FtF are able to at least one of withstand, buffer, and sink the heat from the friction caused from the high RPM use.

Under the higher RPMs the disclosed, the FtF clutch performed beyond the failure of the arrangement shown in FIGS. 7A and 7B. There was still some heat deformation 259 at the leading edge 257 but it did not result in failure. Moreover, in testing the FtF clutch had a maximum torque limit of 50 inch-pounds before it degraded and eventually failed. That is a 2.5 times improvement from the traditional arrangement. Further, the disclosed FtF clutch operated at about 600 RPM at at least 20 inch-pounds. At this same force, the traditional device failed.

While the method and apparatus have been described in terms of what are presently considered to be the most practical and preferred implementations, it is to be understood that the disclosure need not be limited to the disclosed implementations. It is intended to cover various modifications and similar arrangements included within the spirit and scope of the claims, the scope of which should be accorded the broadest interpretation so as to encompass all such modifications and similar structures. The present disclosure includes any and all implementations of the following claims.

It should also be understood that a variety of changes may be made without departing from the essence of the disclosure. Such changes are also implicitly included in the description. They still fall within the scope of this disclosure. It should be understood that this disclosure is intended to yield a patent covering numerous aspects of the disclosure both independently and as an overall system and in both method and apparatus modes.

Further, each of the various elements of the disclosure and claims may also be achieved in a variety of manners. This disclosure should be understood to encompass each such variation, be it a variation of an implementation of any apparatus implementation, a method or process implementation, or even merely a variation of any element of these.

Particularly, it should be understood that as the disclosure relates to elements of the disclosure, the words for each element may be expressed by equivalent apparatus terms or method terms—even if only the function or result is the same.

Such equivalent, broader, or even more generic terms should be considered to be encompassed in the description of each element or action. Such terms can be substituted where desired to make explicit the implicitly broad coverage to which this disclosure is entitled.

It should be understood that all actions may be expressed as a means for taking that action or as an element which causes that action.

Similarly, each physical element disclosed should be understood to encompass a disclosure of the action which that physical element facilitates.

Any patents, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in at least one of a standard technical dictionary recognized by artisans and the Random House Webster's Unabridged Dictionary, latest edition are hereby incorporated by reference.

Finally, all referenced listed in the Information Disclosure Statement or other information statement filed with the application are hereby appended and hereby incorporated by reference; however, as to each of the above, to the extent that such information or statements incorporated by reference might be considered inconsistent with the patenting of this/these disclosure(s), such statements are expressly not to be considered as made by the applicant(s).

In this regard it should be understood that for practical reasons and so as to avoid adding potentially hundreds of claims, the applicant has presented claims with initial dependencies only.

Support should be understood to exist to the degree required under new matter laws—including but not limited to United States Patent Law 35 USC 132 or other such laws—to permit the addition of any of the various dependencies or other elements presented under one independent claim or concept as dependencies or elements under any other independent claim or concept.

To the extent that insubstantial substitutes are made, to the extent that the applicant did not in fact draft any claim so as to literally encompass any particular implementation, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative implementations.

Further, the use of the transitional phrase "comprising" is used to maintain the "open-end" claims herein, according to traditional claim interpretation. Thus, unless the context requires otherwise, it should be understood that the term "compromise" or variations such as "comprises" or "comprising", are intended to imply the inclusion of a stated element or step or group of elements or steps but not the exclusion of any other element or step or group of elements or steps.

Such terms should be interpreted in their most expansive forms so as to afford the applicant the broadest coverage legally permissible.

The invention claimed is:

1. A motor powered torque-limiting driver comprising:
    a cylindrical body (6) having a fortified connector mount (500) on one end and a nose cone (8) at the other end;
    a drive shaft (600) mounted in said connector mount;
    wherein the cylindrical body contains:
        an upper cylindrical shank (150) having a face-to-floor crown gear (250) around an axial bore (160);
        a lower cylindrical shank (100) having a face-to-floor crown gear (200) around a drive socket (9);
        a shaft (14) having a tip (12) a drive connection (16) and a threading (17) engaged within the drive socket of the lower cylindrical shank, the shaft extending through the axial bore;
        a nut (25A) of a size and thread to mount on said threading; and,
        a spring (22) between the upper cylindrical shank and nut, wherein the spring is configured to apply a force across the upper cylindrical shank and the lower cylindrical shank, and wherein the spring is connected via the threading to the nut;
    wherein the upper cylindrical shank and the lower cylindrical shank engage for relative rotation when a motor applies rotational force to the drive shaft; and,
    wherein the upper cylindrical shank and the lower cylindrical shank disengage when a predetermined torque limit is exceeded.

2. The motor powered driver of claim 1, further comprising:
    a neck (25C) and a shoulder (25B) integral to the nut of a diameter larger than said spring's inner diameter; and,
    the neck extending below said shoulder of a diameter smaller than said spring's inner diameter.

3. The torque-limiting driver of claim 2 wherein said fortified connector mount further comprises a drive cap (2) having pairs of opposing force buttressing ribs (515/515') affixed at one edge to an annular wall (514) surrounding the fortified connector mount (500) and at another edge affixed to a flat top (512) of the drive cap.

4. The torque-limiting driver of claim 3, wherein the driver applies a force of between about 20 inch-pounds and about 50 inch-pounds, at an RPM exceeding 350RPM.

5. The torque-limiting driver of claim 3, wherein the driver applies a force of between about 20 inch-pounds and about 50 inch-pounds, at an RPM exceeding about 500 RPM.

6. The torque-limiting driver of claim 3, wherein the driver applies a force of between about 20 inch-pounds and about 50 inch-pounds, at an RPM exceeding about 500 RPM.

7. The torque-limiting driver of claim 3, wherein the driver applies a force of between about 20 inch-pounds and about 50 inch-pounds at an RPM between about 250 RPM and about 600 RPM.

8. The torque-limiting driver of claim 1, wherein a force provided by the spring securely maintains the drive connection of the shaft engaged within the drive socket of the lower cylindrical shank.

9. The torque-limiting driver of claim 1, further comprising at least two washers (20/21) between the spring and the upper cylindrical shank.

10. The torque-limiting driver of claim 1, further comprising a washer (35) between the lower cylindrical shank and the body.

11. The torque-limiting driver of claim 1, comprising at least one washer between the spring and the nut.

12. A motor powered torque-limiting driver comprising:
a cylindrical body (6) having a fortified connector mount (500) on one end and a nose cone (8) at the other end, the cylindrical body containing an upper cylindrical shank (150) having a face-to-floor crown gear (250) around an axial bore (160);
at least one pair of force buttressing ribs disposed on the fortified connector mount;
a drive channel (550) formed in the fortified connector mount with a square configuration having corners (555), the drive channel formed axial and centered relative to the axial bore and having a size to accept a tool or shaft;
wherein said force buttressing ribs each have a bottom (580) at a flat top (512) of the fortified connector mount and each force buttressing rib has a support edge (590) at the annular wall (514) of the fortified connector mount (500);
a drive shaft (600) mounted in said drive channel;
a lower cylindrical shank (100) having a face-to-floor crown gear (200) around a drive socket (9);
a shaft (14) having a tip (12) a drive connection (16) and a threading (17), with the drive connection engaged within the drive socket of the lower cylindrical shank, the shaft extending through the axial bore;
a nut (25A) of a size and thread to mount on said threading;
a spring (22) between the upper cylindrical shank and nut, wherein the spring is configured to apply a force across the upper cylindrical shank and the lower cylindrical shank, wherein the spring is connected via the threading to the nut;
wherein the upper cylindrical shank and the lower cylindrical shank engage for relative rotation when a motor applies rotational force to the drive shaft; and,
wherein the upper cylindrical shank and the lower cylindrical shank disengage when a predetermined torque limit is exceeded.

13. The torque-limiting driver of claim 12, wherein the driver applies a force of between about 20 inch-pounds and about 50 inch-pounds at an RPM between about 250 RPM and about 600 RPM.

* * * * *